US012806131B2

(12) United States Patent
Deruddre et al.

(10) Patent No.: US 12,806,131 B2
(45) Date of Patent: Nov. 24, 2026

(54) AQUEOUS PERSONAL CARE COMPOSITIONS COMPRISING CARBOXYMETHYL CELLULOSE (CMC) HAVING AN OPTIMIZED DEGREE OF SUBSTITUTION

(71) Applicant: ISP INVESTMENTS LLC, Wilmington, DE (US)

(72) Inventors: Karine Deruddre, Villeneuve Loubet (FR); Marie-Aude Gidel Soury-Lavergne, Mougin (FR); Clémence Métro, Nice (FR); Hani M. Fares, Somerset, NJ (US)

(73) Assignee: ISP Investments LLC, Wilmington, DE (US)

( * ) Notice: Subject to any disclaimer, the term of this patent is extended or adjusted under 35 U.S.C. 154(b) by 341 days.

(21) Appl. No.: 18/554,377

(22) PCT Filed: Apr. 6, 2022

(86) PCT No.: PCT/US2022/023617
§ 371 (c)(1),
(2) Date: Oct. 6, 2023

(87) PCT Pub. No.: WO2022/216789
PCT Pub. Date: Oct. 13, 2022

(65) Prior Publication Data

US 2024/0216256 A1 Jul. 4, 2024

Related U.S. Application Data

(60) Provisional application No. 63/171,266, filed on Apr. 6, 2021.

(51) Int. Cl.
*A61K 8/73* (2006.01)
*A61Q 19/00* (2006.01)

(52) U.S. Cl.
CPC .............. *A61K 8/731* (2013.01); *A61Q 19/00* (2013.01); *A61K 2800/594* (2013.01); *A61K 2800/74* (2013.01); *A61K 2800/805* (2013.01)

(58) Field of Classification Search
CPC .............. A61K 8/731; A61K 2800/594; A61K 2800/74; A61K 2800/805; A61K 8/0241; A61K 8/73; A61K 8/732; A61K 8/8147; A61K 8/8152; A61K 8/8164; A61K 8/8182; A61Q 19/00; A61Q 1/08; A61Q 1/10; A61Q 5/02; A61Q 5/12; A61Q 9/00; A61Q 17/04
See application file for complete search history.

(56) References Cited

U.S. PATENT DOCUMENTS

| | | | |
|---|---|---|---|
| 2,495,767 A | | 1/1950 | David |
| 3,842,168 A | | 10/1974 | Colodney |
| 4,401,813 A | * | 8/1983 | Lowell et al. |
| 4,525,585 A | | 6/1985 | Taguchi et al. |
| 4,883,537 A | | 11/1989 | Burdick |
| 5,691,060 A | | 11/1997 | Levy |
| 6,497,891 B2 | | 12/2002 | Bara |
| 7,488,470 B2 | | 2/2009 | Nguyen et al. |
| 8,556,992 B2 | | 10/2013 | Degeorge et al. |
| 8,940,680 B2 | | 1/2015 | Bernard et al. |
| 9,162,007 B2 | | 10/2015 | Bitis et al. |
| 9,181,659 B2 | | 11/2015 | Morrison et al. |
| 9,364,690 B2 | | 6/2016 | Lorant et al. |
| 9,801,804 B2 | | 10/2017 | Tan et al. |
| 9,884,003 B2 | | 2/2018 | Tan et al. |
| 9,993,406 B2 | | 6/2018 | Manneck et al. |
| 10,039,939 B2 | | 8/2018 | Xavier et al. |
| 10,111,824 B2 | | 10/2018 | Lee et al. |
| 10,238,585 B2 | | 3/2019 | Ishida et al. |
| 10,912,727 B2 | | 2/2021 | Biato et al. |
| 2003/0035783 A1 | | 2/2003 | Birkel et al. |
| 2012/0040065 A1 | | 2/2012 | Adden et al. |
| 2012/0207689 A1 | | 8/2012 | Konno et al. |
| 2014/0370180 A1 | | 12/2014 | Tan et al. |
| 2016/0101887 A1 | | 4/2016 | McKinnon et al. |

(Continued)

FOREIGN PATENT DOCUMENTS

| | | | | |
|---|---|---|---|---|
| CN | 117377455 A | * | 1/2024 | ............. A61Q 19/00 |
| GB | 1376091 A | | 12/1974 | |

(Continued)

OTHER PUBLICATIONS

International Search Report, PCT /US2022/023617 published on Oct. 13, 2022.

(Continued)

*Primary Examiner* — Robert A Wax
*Assistant Examiner* — Kimberly Barber
(74) *Attorney, Agent, or Firm* — Aseem Mehta; Nathalie Tietcheu

(57) ABSTRACT

Disclosed is an aqueous personal care composition, particularly oil-in-water, water-in-oil skin care emulsion or a suspension composition comprising 0.1 to 10 wt. % of low substituted carboxymethyl cellulose (CMC) alone or in combination with 0.01 to 10 wt. % of at least one nature derived or at least one fossil derived polymer, 0.01 to 60 wt. % of at least one personal care additive, and water; wherein, the low substituted carboxymethyl cellulose has an average degree of carboxymethyl substitution (DS) per anhydroglucose unit is in the range of from about 0.5 to about 0.7, and wherein, the low substituted carboxymethyl cellulose is readily biodegradable.

16 Claims, 4 Drawing Sheets

(56) References Cited

U.S. PATENT DOCUMENTS

| | | | |
|---|---|---|---|
| 2016/0235634 | A1 | 8/2016 | Sato et al. |
| 2017/0181948 | A1* | 6/2017 | Wu |
| 2019/0231665 | A1 | 8/2019 | Gregolin et al. |

FOREIGN PATENT DOCUMENTS

| | | | |
|---|---|---|---|
| JP | 3692007 | B2 | 9/2005 |
| JP | 5962567 | B2 | 8/2016 |
| JP | 2019-172664 | A2 | 10/2019 |
| JP | 2020-182904 | A2 | 11/2020 |
| WO | WO2015097033 | A1 | 7/2015 |
| WO | WO2020164769 | A1 | 8/2020 |
| WO | WO2022216789 | A1 | 10/2022 |
| WO | WO2022266161 | A1 | 12/2022 |

OTHER PUBLICATIONS

Vanginkel C. G. et al., "The biodegradability and nontoxicity of carboxymethyl cellulose (DS 0.7) and intermediates", Environmental Toxicology and Chemistry, 1996, vol. 15, issue 3, pp. 270-274; retrieved from the Internet:< DOI: 10.1002/etc.5620150307 >; see entire document, especially, p. 270-273.

Ashland_BULLETIN_VC-5674.

ProductGradesAshlandXP093238862URLhttps://www.ashland.com/file_source/Ashland/Industries/Pharmaceutical/Articles/PC-11608.11_Pharma_Product_Grades.pdf.

* cited by examiner

SUSPENSION STUDIES OF COMMERCIAL CMC vs. INVENTIVE CMC SAMPLE GRADES

After 24 Hrs at RT 1.5% Sample Grade 1.5% Commercial CMC 1% Sample Grade 0.5% Sample Grade After 3 months at 45°C 1.5% Sample Grade After 2 months at 45°C 1.5% Sample Grade

VISCOSITY DATA OF CMC - CETYL HEC COMBINATION SAMPLES

AQUEOUS PERSONAL CARE COMPOSITIONS COMPRISING CARBOXYMETHYL CELLULOSE (CMC) HAVING AN OPTIMIZED DEGREE OF SUBSTITUTION

FIELD OF THE INVENTION

The present disclosure relates to an aqueous personal care composition, particularly skin care composition comprising carboxymethyl cellulose (CMC) having optimized degree of substitution (DS) and process for preparing the same.

BACKGROUND OF THE INVENTION

Conventionally, personal care products are used for improved moisturization, absorption, feel good factor or enhanced appearance. It is also desired that these products should not be sticky in nature, resist to varied temperatures, provide varying degrees of emolliency, and retain moisture. Further, care products should exhibit good rheology i.e. flow in the right way, be easily picked up, or rubbed onto the skin. Many natural and synthetic polymers have been used to improve rheology in personal care products. Viscosity and the degree of substitution (DS) of polymers in solutions determine their functionality. Carboxymethyl cellulose (CMC) has wide range of molecular weights, viscosity grades, and is odorless, tasteless, and chemically stable. The physical properties of CMC, particularly viscosity and solubility, largely depend on the degree of substitution (the number of reactive carboxymethyl groups and nature of the substituent group). CMC functions as a stabilizer, protective colloid, bulking agent, and water-retention agent. The Cosmetic Ingredient Review (CIR) Expert Panel has reviewed the available CMC toxicological data and concluded that CMC is safe as a cosmetic ingredient.

U.S. Pat. No. 2,495,767 assigned to John David Reid and George C. Daul discloses continuous fibres spun from carboxymethyl cellulose having a DS between 0.5 and 1.0.

U.S. Pat. No. 4,525,585 assigned to Diacel Chemical Industries Ltd. discloses sodium carboxymethyl cellulose with average degree of substitution of 0.4 to 1.6.

U.S. Pat. No. 9,181,659 assigned to CP Kelco OY discloses carboxymethyl alkali solutions having a DS of less than about 0.9 for use in high solid paper coating and barrier materials.

However, lower the degree of substitution in carboxymethyl cellulose (CMC), less is the solubility in water. Higher the degree of substitution, less stable is the emulsion or suspensions prepared using CMC's. In such instances, emulsion stability and rheology behavior are compromised making the product less suitable for personal care application. Therefore, there is a need in the art for a personal care emulsion or suspension having carboxymethyl cellulose with an optimized degree of substitution wherein solubility in aqueous solutions and stability are not compromised.

SUMMARY OF THE INVENTION

The primary aspect of the present application is directed to an aqueous personal care composition comprising: (a) 0.1 to 10.0 wt. % of low substituted carboxymethyl cellulose (CMC) alone or in combination with 0.01 to 10.0 wt. % of at least one nature derived polymer or at least one fossil derived polymer; (b) 0.01 to 60 wt. % of at least one personal care additive; and (c) water; wherein, the low substituted carboxymethyl cellulose has an average degree of carboxymethyl substitution (DS) per anhydroglucose unit, in the range of from about 0.5 to about 0.7; wherein, the low substituted carboxymethyl cellulose is readily biodegradable.

Another aspect of the present application provides an aqueous skin care suspension composition comprising: (a) 0.1 to 10.0 wt. % of low substituted carboxymethyl cellulose (CMC) alone or in combination with 0.01 to 10.0 wt. % of at least one nature derived polymer or at least one fossil derived polymer; (b) 0.01 to 60 wt. % of at least one skin care additive; and (c) water; wherein, the low substituted carboxymethyl cellulose has an average degree of carboxymethyl substitution (DS) per anhydroglucose unit, in the range of from about 0.5 to about 0.7; wherein, the low substituted carboxymethyl cellulose is readily biodegradable.

Another aspect of the present application provides an aqueous skin care oil-in-water or water-in-oil emulsion composition comprising: (a) 0.1 to 10.0 wt. % of low substituted carboxymethyl cellulose (CMC) alone or in combination with 0.01 to 10.0 wt. % of at least one nature derived polymer or at least one fossil derived polymer; (b) 0.01 to 60 wt. % of at least one skin care additive; and (c) water; wherein, the low substituted carboxymethyl cellulose has an average degree of carboxymethyl substitution (DS) per anhydroglucose unit, in the range of from about 0.5 to about 0.7, wherein, the low substituted carboxymethyl cellulose is readily biodegradable.

Another aspect of the present application provides a process for preparing an aqueous personal care composition, the process comprising: (a) considering powder particles comprising low substituted carboxymethyl cellulose (CMC) alone or in combination with at least one nature derived polymer or fossil derived polymer; (b) dispersing the polymer powder in water under continuous mixing; and (c) obtaining the homogenous aqueous composition.

BRIEF DESCRIPTION OF DRAWINGS

In addition to the cited advantages and objects of the disclosure, one or more descriptions of the disclosure briefly summarized can be added by reference to certain embodiments thereof which are illustrated in the appended drawings. These drawings form part of the specification. However, it is to be noted that the appended drawings illustrate preferred embodiments of the disclosure and therefore are not limiting in their scope.

DETAILED DESCRIPTION OF THE INVENTION

Figure 1:
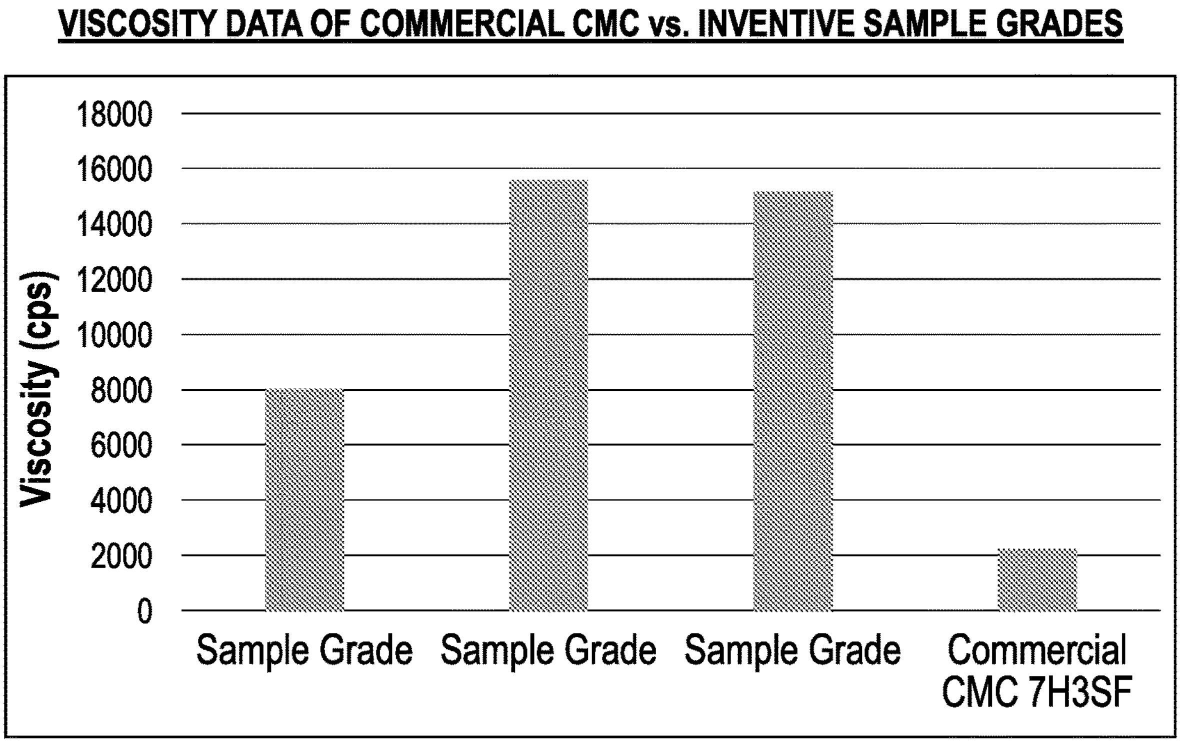
FIG. 1 illustrates viscosity data of comparative CMC vs. inventive CMC sample grades.

The technical solutions of the present disclosure will be described clearly and better understood in combination with specific embodiments below, but those skilled in the art will understand that embodiments described below are part of embodiments of the present disclosure but not all of them and are only used for illustration of the present disclosure and should not be considered as limiting the scope of the disclosure. If any specific condition or process are not indicated in the examples, it is to be understood that the conditions are conventionally used by the manufacturer and is commercially available.

As utilized in accordance with the disclosure, the following terms, unless otherwise indicated, shall be understood to have the following meanings.

Unless otherwise defined herein, technical terms used in connection with the disclosed and/or claimed inventive concept(s) shall have the meanings that are commonly understood by those of ordinary skill in the art. Further, unless otherwise required by the context, singular terms shall include pluralities and plural terms shall include the singular.

The singular forms "a," "an," and "the" include plural forms unless the context clearly dictates otherwise specified or clearly implied to the contrary by the context in which the reference is made. The term "Comprising" and "Comprises of" includes the more restrictive claims such as "Consisting essentially of" and "Consisting of".

For purposes of the following detailed description, other than in any operating examples, or where otherwise indicated, numbers that express, for example, quantities of ingredients used in the specification and claims are to be understood as being modified in all instances by the term "about". The numerical parameters set forth in the specification and attached claims are approximations that may vary depending upon the desired properties to be obtained in carrying out the invention.

All percentages, parts, proportions and ratios as used herein, are by weight of the total composition, unless otherwise specified. All such weights as they pertain to listed ingredients are based on the active level and, therefore; do not include solvents or by-products that may be included in commercially available materials, unless otherwise specified.

All publications, articles, papers, patents, patent publications, and other references cited herein are hereby incorporated herein in their entirety for all purposes to the extent consistent with the disclosure herein.

As used herein, the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results.

As used herein, the term "alkyl polyglucosides" is referred in abbreviation form "APG" throughout the specification and refers to non-ionic surfactants. Few non-limiting examples include cocoglucoside, decyl Glucoside, and dodecyl glucoside.

As used herein, the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "optimized carboxymethyl cellulose CMC", "low substituted carboxymethyl cellulose", "carboxymethyl cellulose", "CMC", "cellulose gum" or "bio cellulose" or "bio gel" or "sample grade" or "inventive sample" used throughout the specification including drawings are interchangeable and refer to sodium salt of carboxymethyl cellulose having a degree of substitution in the range of 0.5 to 0.7.

As used herein, the term "cosmetically acceptable" refers to molecular entities regarded as safe, approved by regulatory body, listed in pharmacopoeia for use in topical contact with tissues (e.g., the skin) without undue toxicity, incompatibility, instability, irritation, allergic response, or the like. This term is not intended to limit the composition it describes as for use solely as a cosmetic (e.g., the composition may be used as a pharmaceutical).

As used herein, the term "degree of substitution (DS)" or "substituted degree" or "substitution degree" generally refers to carboxymethyl cellulose with the average number of carboxymethyl groups substituted per unit of anhydroglucose. Each anhydroglucose (β-glucopyranose) unit has three reactive (hydroxyl) groups, so theoretically DS value can be in the range from zero (cellulose itself) to three (fully substituted cellulose). The position and DS were measured using NMR by the identification of protons and carbon shift of methyl groups in the anhydroglucose unit and anhydride groups.

As used herein, the term "polymer" refers to a compound comprising repeating structural units (monomers) connected by covalent chemical bonds. Polymers may be further derivatized, crosslinked, grafted or end-capped. Non-limiting examples of polymers include copolymers, terpolymers, tetra polymers, quaternary polymers, and homologues. The term "copolymer" refers to a polymer consisting essentially of two or more different types of monomers polymerized to obtain said copolymer.

As used herein, the term "personal care composition" and "cosmetics" refer to compositions intended for use on or in human body such as skin, hair, oral including those to alter the color and appearance of skin and hair.

As used herein, the term "viscosity of a solution" or "average viscosity" refers to measure of its resistance to gradual deformation by shear stress, which is due to intermolecular cohesive forces. These forces are affected by some factors such as concentration, temperature, or degree of substitution.

As used herein, the term 'rheology' refers to "the science or study of how things flow", a requisite for personal care products.

As used herein, the term "sample grade" or "sample" referred in specification and drawings relate to inventive sodium carboxymethyl cellulose having degree of substitution of 0.5 to 0.7.

As used herein, the term 'xanthan gum' refers to a polysaccharide gum industrially capable of producing a change in rheology of a liquid. Any commercially available xanthan gum may be used in the present invention. The suitable commercial xanthan gum includes, but not limiting to, Xanthan Gum®, (Kelzan® from Kelco) or Veegum® (from R. T. Vanderbilt).

Synthetic rheology modifiers (such as carbomer) have traditionally been used to thicken and stabilize skin care emulsions efficiently with appealing aesthetics. Existing natural rheology modifiers typically have very poor aesthetics, making it difficult to create the natural, sustainable formulations consumers want developed through our market leading expertise in sustainably sourced cellulosics, combined with our rheology modification experience, present inventors attempt to introduce a sustainable alternative.

In one non-limiting embodiment, the present disclosure is directed to an aqueous personal care composition comprising: (a) 0.1 to 10 wt. % of low substituted carboxymethyl cellulose (CMC) alone or in combination with 0.01 to 10 wt. % of at least one nature derived polymer or at least one fossil derived polymer; (b) 0.01 to 60 wt. % of at least one personal care additive; and (c) water; wherein, the low substituted carboxymethyl cellulose has an average degree of carboxymethyl substitution (DS) per anhydroglucose unit, in the range of from about 0.5 to about 0.7, wherein, the low substituted carboxymethyl cellulose is readily biodegradable.

CMC is a biodegradable, highly compatible anionic polymer obtained from cellulose (naturally sourced from cotton linters, wood pulp, or other cellulosic compounds) by substitution of at least a portion of the hydroxyl groups in cellulose molecule for carboxymethyl ether groups.

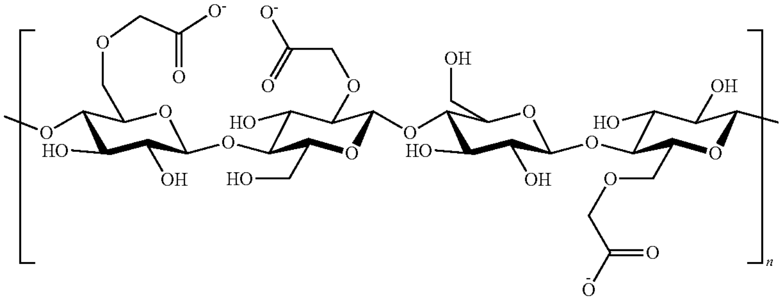

Carboxymethyl cellulose is commercially (CMC) obtained by alkalization reaction of cellulose with sodium mono chloroacetate and has degree of substitution (DS) in the range of 0.4 to 1.3. CMC is completely soluble at DS above 0.4 and hydro affinity of CMC increases with increasing DS, while this polymer is swellable but insoluble below 0.4.

In another non-limiting embodiment, the inventive cellulose is a polycarboxymethyl ether of cellulose and is spontaneously converted to the sodium salt in alkaline solution (CMC sodium). The cellulose gum i.e. sodium carboxymethyl cellulose has degree of substitution in the range of 0.5 to 0.7. As per biodegradability standards, OECD guidelines, 301D assay with a CMC of similar structure and physical properties, 71% biodegradation was observed after 28 days. The present "cellulose gum" is a bio cellulose assessed as readily biodegradable.

The carboxymethyl cellulose is present in a concentration range of from about 0.1 to about 10.0 wt. % of the total personal care composition. The nature derived polymer or fossil derived polymer is present in a concentration range of from about 0.01 to about 10.0 wt. % of the total personal care composition. The care composition additionally comprises 0.01 to 10 wt. % of care additive and water.

In another non-limiting embodiment, the low substituted carboxymethyl cellulose is present in the form of a solid particulate or a powder, has high viscosity with an average viscosity range of from about 2500 to about 8500 cps, or from about 8500 to 16000 cps, or from about 16000 to about 120000 cps in 1% aqueous solution as measured by Brookfield, spindle A, speed 5.

Molecular weight of cellulose compounds is determined by GPC/SEC analysis. Gel Permeation Chromatography (GPC), also referred to as Size Exclusion Chromatography (SEC), is a valuable tool for the characterization of molecular weight, average molecular weight, and molecular weight distribution for polymers. For purposes of this invention, all molecular weights are given in weight average molecular weight (Mw) and measured in Daltons (Da). In an embodiment of this invention, the weight average molecular weight of the carboxymethyl cellulose will be in the range of from about 1000,000 to about 2000,000 Daltons.

Nature derived polymers used in the compositions of this invention can be selected from the group including, but not limited to xanthan gum, guar gum, carob gum, konjac gum, sclerotium gum, acacia gum, cellulose gum, pullulan, microcrystalline cellulose, sodium carboxymethyl starch, hydroxypropyl starch phosphate, hydrophobically modified hydroxyethyl cellulose (HMHEC) such as cetearyl hydroxyethyl cellulose, *Caesalpinia spinosa* gum, carrageenan, dehydroxanthan gum, potato starch modified, glucomannan, magnesium aluminium silicate, bentonite, corn starch modified, polyester based polymer and gellan Gum. Preferably, nature derived polymer is xanthan gum. Xanthan is a polysaccharide with polyglucose as main polymer backbone with 3-unit acetylated side chains including glucose, glucuronic acid, typically present as a mixed potassium, sodium and calcium salt, and mannose residues. Xanthan polymers are typically obtained from bacterial fermentations, particularly of *Xanthomonas campestris* and related microorganisms.

Fossil derived polymers useful in the practice of this invention include an acrylate based, methacrylate based polymer, maleic anhydride based polymer, polyester based, polyurethane based polymer or a vinyl pyrrolidone based polymer. Suitable acrylates or alkyl acrylates includes but not limited to (meth)acrylic acid, methyl (meth)acrylate, ethyl (meth)acrylate, propyl (meth)acrylate, isopropyl (meth)acrylate, butyl (meth)acrylate, amyl (meth)acrylate, isobutyl (meth)acrylate, t-butyl (meth)acrylate, pentyl (meth)acrylate, isoamyl (meth)acrylate, hexyl (meth)acrylate, heptyl (meth)acrylate, octyl (meth)acrylate, isooctyl (meth)acrylate, 2-ethylhexyl (meth)acrylate, nonyl (meth) acrylate, decyl (meth)acrylate, isodecyl (meth)acrylate, undecyl (meth)acrylate, dodecyl (meth)acrylate, lauryl (meth)acrylate, octadecyl (meth)acrylate, and stearyl (meth) acrylate; alkoxy alkyl (meth)acrylates, particularly d-alkoxy d-alkyl (meth)acrylates, such as butoxy ethyl acrylate and ethoxyethoxyethyl acrylate; aryloxy alkyl (eth)acrylate, particularly aryloxy C4 alkyl (meth)acrylates, such as phenoxyethyl acrylate, single and multi-ring cyclic aromatic or non-aromatic acrylates such as cyclohexyl acrylate, benzyl acrylate, dicyclopentadiene acrylate, dicyclopentanyl acrylate, tricyclodecanyl acrylate, bornyl acrylate, isobornyl acrylate, alcohol-based (meth)acrylates such as polyethylene glycol monoacrylate, polypropylene glycol monoacrylate, methoxy ethylene glycol acrylate, methoxypolypropylene glycol acrylate, methoxy polyethylene glycol acrylate, ethoxydiethylene glycol acrylate, and various alkoxylated alkylphenol acrylates such as ethoxylated (4) nonylphenol acrylate, amides of (meth)acrylic acid such as diacetone acrylamide, isobutoxymethyl acrylamide, t-octyl acrylamide.

Further, fossil derived polymers include lactams not limiting to N-vinyl pyrrolidone, N-vinyl caprolactam, N-methyl-pyrrolidone, N-hydroxymethyl pyrrolidone, N-hydroxyethyl pyrrolidone, and N-hydroxypropyl pyrrolidone. Representative anhydrides include formic anhydride, succinic anhydride, maleic anhydride and acetic anhydride. Preferred fossil derived polymers include methyl vinyl ether/maleic anhydride copolymer crosslinked with decadiene and polyacrylic acid.

Suitable preservatives used in the present composition can be natural preservatives selected from the group comprising cinnamaldehyde, organic acids, raspberry ketone, thymol, eugenol, citral, monolaurin, garcinol, and supercritical fluid extracts of *Magnolia officinalis* comprising magnolol and honokiol, or synthetic selected from the group comprising parabens, phenoxyethanol, formaldehyde, cetyl pyridinium chloride, benzethonium chloride, benzalkonium chloride, polyaminopropyl biguanide, 2-bromo-2-nitro-1,3-diol, iodopropynyl butylcarbamate (IPBC), imidazolidinyl urea, diazolidinyl urea, benzoic and sorbic acids in benzyl alcohol. Parabens include methyl paraben, ethyl paraben, and propyl paraben.

Suitable surfactants used in the present composition can be non-ionic or ionic which are natural and synthetic in nature. Non-ionic surfactants include alkyl polyglucosides, also referred to as "APG". Alkyl Polyglucosides are surfactants of natural origin essentially comprising starch and coconut oil; and 100% biodegradable.

Suitable moisturizers employed in the present composition would include glycols, glycerols, propylene glycol, diethylene glycol monoethyl ether, sorbitol, sodium salt of pyroglutamic acid, glycerol, glycerol derivatives, glycerin, trehalose, sorbitol, maltitol, dipropylene glycol, 1,3-butylene glycol, sodium hyaluronate, and the like.

A perfume or fragrance obtained from natural or synthetic source can be employed in the present personal care composition. The fragrance may be used along with a suitable solvent, diluents or carrier. Fragrances may be added in any conventionally known method, for example, admixing to a composition or blending with other ingredients used to form a composition, in amounts which are found to be useful to increase or impart the desired scent characteristics to the disinfectant or cleaning compositions. Fragrances for the present application can be one or more selected from the following non-limiting group of compounds such as essential oils, absolutes, resinoids, resins, concretes, hydrocarbons, alcohols, aldehydes, ketones, ethers, acids, esters, acetals, ketals, nitriles, including saturated and unsaturated compounds and aliphatic, carboxylic and heterocyclic compounds. Preferred perfumes or fragrances used in the application include Citronellol, Hexyl cinnamal, Limonene, *Jasminum grandiflorum* flower extract, Geraniol, and Linalool.

In another non-limiting embodiment, the current personal care composition is formulated into a hair-care product, a shampoo, a hair conditioner, leave in and rinse off conditioner, a styling hair composition, a hair perming product, a hair relaxant, a hair straightener, a hair spray and lacquer, a permanent hair dyeing system, a hair styling mousse, a hair gel, a semi-permanent hair dyeing system, a temporary hair dyeing system, a hair bleaching system, a permanent hair wave system, a hair setting formulation, a liquid soap, a bar soap, a fragrance and/or odoriferous ingredients consisting preparation, a deodorizing and antiperspirant preparation, a body oil, a body lotion, a body gel, a treatment cream, a body cleaning product, a skin protection ointment, a shaving and aftershave preparation, a skin powder, a lipstick, a foundation, a nail varnish, an eye shadow, a mascara, a dry and moist make-up, a blush or a blusher, a powder, a depilatory agent, a leave-on skin lotion and cream, a shower gel, a toilet bar, a sunless tanner, a sunscreen lotion, a sunscreen spray, a sunscreen cream, a hair styling gel, a serum, a mask and a tooth paste.

In another non-limiting embodiment, the low substituted CMC alone or in combination is used in the preparation of personal care composition in the form of an emulsion, a dispersion, a suspension, a lotion, a cream, a foam, a spray, a gel, a soap bar, a stick, a mask, a pad or a patch.

In another non-limiting embodiment, the personal care formulations comprising low substituted carboxymethyl cellulose have an average viscosity from about 20,000 to about 30,000 cps, or from about 30,000 to about 50,000 cps, or from about 40,000 to about 60,000 cps, or from about 50,000 to about 70,000 cps, or from about 110,000 to 130,000 cps, or from about 150,000 to about 200,000 cps, or from about 200,000 to about 250,000 cps, or from about 220,000 to about 260,000 cps.

The emulsion is an oil-in-water emulsion or a water-in-oil emulsion. Current oil-in-water emulsion is stable, could impart high viscosity and provides aesthetic feel and sensory attributes to the consumer. When used in personal care applications, various additives are employed to provide varied additional benefits to the final personal care product.

In another non-limiting embodiment, the present disclosure is directed to an aqueous skin care suspension composition comprising: (a) 0.1 to 10.0 wt. % of low substituted carboxymethyl cellulose (CMC) alone or in combination with 0.01 to 10.0 wt. % of at least one nature derived polymer or fossil derived polymer; (b) 0.1 to 60.0 wt. % of at least one skin care additive; and (c) water; wherein, the low substituted carboxymethyl cellulose has an average degree of carboxymethyl substitution (DS) per anhydroglucose unit, in the range of from about 0.5 to about 0.7.

Suspending agents are employed to suspend particles in aqueous solutions. Those particles could be selected from beads, captivates which encapsulate active material. These encapsulates are a series of small particles that contain an active ingredient, or core material, surrounded by a shell and are produced using complex coacervation process. They differ in capsule wall thickness, color, capsule size and core material. These encapsulates enhance visual effect, delivers flavor, provides texture, sensory signals, isolates and protects ingredients, suspends sugar, salts, silica and other exfoliant agents. Preferred encapsulates are captivates GL and captivates HC encapsulates. Captivates™ hc encapsulates are a series of small particles, in sizes ranging from 250 μm to 3,000 μm, that contain an active ingredient, or core material, surrounded by a shell produced using a complex coacervation process. Capsule wall thickness, color, capsule size and core material can be customized. Captivates™ gl encapsulates are a series of small particles, in sizes ranging from 5 μm to 2,000 μm, that contain material dispersed in a continuous matrix. These microbeads are made using JettCutter™ technology, which forms a hydrogel matrix that can entrap insoluble powders, oils and water-soluble actives.

Several other components can be included in the formulation to improve its properties and function. For that purpose, one or more moisturizers selected from the group comprising Aloe barbadensis leaf juice (CMC can resist electrolytes) and glycerin, one or more antioxidants selected from the group comprising *Rubus idaeus* (Raspberry) seed oil, citrus unshiu peel extract and caffeine extract, one or more conditioning agents selected from glycerin or ethylhexylglycerin; one or more boosters for preservatives selected from raspberry ketone, 1,2-hexanediol and phenoxyethanol can be added to improve the overall performance of the product.

Hydrogel is a multi-functional sensory enhancer for creating moisturizing skincare formulations easily. Present application includes natural ingredients or nature-derived ingredients such as Lubrajel™—INCI name—Water (and) Glycerin (and) Sodium PCA (and) Erythritol (and) *Chondrus crispus* (and) Xanthan Gum, Aloe Barbadensis juice powder derived from desert plant Aloe Vera in formulations for anti-inflammatory and effective skin moisturizer effects.

In another non-limiting embodiment, the present disclosure is directed to an aqueous skin care oil-in-water or water-in-oil emulsion composition comprising: (a) 0.1 to 10.0 wt. % of low substituted carboxymethyl cellulose (CMC) alone or in combination with 0.01 to 10.0 wt. % of at least one nature derived polymer or fossil derived polymer; (b) 0.01 to 60.0 wt. % of at least one skin care additive; and (c) water; wherein, the low substituted carboxymethyl cellulose has an average degree of carboxymethyl substitution (DS) per anhydroglucose unit, in the range of from about 0.5 to about 0.7.

Emulsion systems have two immiscible phases, wherein one phase is dispersed or suspended throughout the other phase. Key feature of a good emulsion is to keep the two phases remain immiscible and not to get separated into two distinct phases. Emulsifiers are used to slow down the separation process. Addition of emulsifiers helps solids to be dispersed in liquids or insoluble liquids with other liquids. These emulsifiers or emulsifying agents are surfactants and are well known in the art. Present disclosure employs anionic, amphoteric, and zwitterionic emulsifiers. Anionic emulsifiers can be selected from the group comprising ethoxylated alkyl sulphates not limiting to alkyl ethoxy carboxylates, alkyl glyceryl ether sulphonates, acyl sarcosinates, alkyl ethoxy sulphosuccinates, alpha-sulphonated fatty acids, their salts and/or esters, ethoxylated alkyl phosphate esters, ethoxylated alkyl glyceryl ether sulfonates, paraffin sulfonates and alkoxy amide sulfonates, alkyl sulphates, alkyl ether sulphates, alkaryl sulphonates, alkanoyl isethionates, alkyl succinates, alkyl sulphosuccinates, N-alkyl sarcosinates, alkyl ether phosphates, alkyl ether carboxylates, alpha-olefin sulphonates, salts of alkyl sulfates, salts of alkylbenzene sulfonates, salts of dialkyl sulfosuccinates, salts of alkyl phosphoric acids, salts of polyoxyethylene alkyl ether sulfates, glycerin monostearate, alkyl amine oxides, sorbitan monopalmitate, polyoxyethylene cetyl ether, polyoxyethylene stearic acid ester, polyoxyethylene sorbitan monolaurate and mixtures thereof. The alkyl and acyl groups generally contain from 6 to 22 carbon atoms and can be unsaturated. Nonionic emulsifiers can be selected from the group comprising alkyl glucosides, alkyl polyglycosides, polyhydroxy fatty acid amides, alkoxylated sugar esters and polyesters, fatty acid amides, condensation products of alkylene oxides and fatty acids, such as alkylene oxide esters of fatty acids and alkylene oxide diesters of fatty acids, condensation products of alkylene oxides and fatty alcohols, such as PEG 40 hydrogenated castor oil, PEG stearate, laureth, PEG laureth ester, PEG stearate ether, steareth 2, isoceteth-20 and oleth-20, condensation products of alkylene oxides and fatty acids and fatty alcohol, wherein the polyalkylene oxide portion is esterified on one end with a fatty acid and etherified on the other end with a fatty alcohol, polyoxyethylene alkyl ethers, polyoxyethylene alkyl phenyl ethers, polyoxyethylene fatty acid esters, sorbitan fatty acid esters, polyoxyethylene sorbitan fatty acid esters, glycerine fatty acid esters and saccharose fatty acid esters and Polysorbate. Amphoteric emulsifiers are selected from group comprising coco ampho carboxypropionate, coco amphocarboxy propionic acid, cocoamphoacetate, cocoamphodiacetate, sodium lauroampho acetate, N-acylamidopropyl-N,N-dimethylammonio betaines and N-acylamidopropyl-N,N'-dimethyl-N'-2-hydroxypropylammonio betaines. Zwitterionic emulsifiers are selected from the group comprising alkyl betaines and amido betaines, sultaines, alkyl glycinates, alkyl carboxyglycinates, alkylamphopropionates, alkylamphoglycintaes, alkyl amidopropyl hydroxy sulfaines, acyl taurates, acyl glutamates and examples of cationic surfactants include ammonium halide compounds, including those having hydrophilic substituents. Examples of ammonium halide compounds are long-chain alkyl trimethyl ammonium chloride, long-chain alkyl benzyl dimethyl ammonium chloride, alkylamine hydrochlorides, alkylamine acetates and di(long-chain alkyl) dimethyl ammonium bromide. Alkyl and acyl groups have from 8 to 19 carbon atoms. Preferred emulsifiers include sunflower phospholipid based, polyethylene glycol (PEG) free vegetable based, lysophosphatidylcholines (LPC) derived from soybean dissolved in glycerin, cetearyl alcohol and cetearyl glucoside, and glyceryl stearate citrate & polyglyceryl-3 stearate & hydrogenated lecithin, polyglyceryl-3 methylglucose distearate, cetearyl alcohol (and) glyceryl stearate (and) jojoba esters (and) *Helianthus annuus* (Sunflower) seed wax (and) sodium stearoyl glutamate (and) water (and) polyglycerin-3, polyglyceryl-3 dicitrate/stearate, stearic acid (and) behenyl alcohol (and) glyceryl stearate (and) myristyl alcohol (and) lauryl alcohol (and) cetyl alcohol (and) palmitic acid (and) lecithin, glyceryl citrate/lactate/linoleate/oleate, polyglyceryl-6 stearate (and) polyglyceryl-6 behenate.

The emulsion further contains water and additional adjuvants commonly used in the cosmetic and/or dermatological fields, including but not limited to preservatives, fragrances, fillers, screening agents, sequestering agents, essential oils, dyes, hydrophilic or lipophilic active agents, lipid vesicles, vitamin B compounds, vitamin E compounds, vitamin C compounds, vitamin D compounds, peptides, sugar amines, protease inhibitors, sunscreens, desquamation agents, chelators, skin lightening compounds, non-vitamin antioxidant radical scavengers, phytosterols, plant hormones, protease inhibitors, tyrosinase inhibitors, anti-inflammatory agents, topical anesthetics, anti-cellulite agents, sunless tanning agents, N-acyl amino acid compounds and derivatives and mixtures thereof. The emulsions of the present disclosure can be used on the skin of the body, neck and face, eyes, etc. including for the skin of young children, and for the removal of make-up, including around the eyes.

In another non-limiting embodiment, the present formulations may employ one or more personal care additives selected from the group consisting of arachidyl alcohol, arachidyl glucoside, allantoin, Aloe Barbadensis leaf juice powder, behenyl Alcohol, bis-stearoxy dimethylsilane, bis-ethyl hexyloxy phenol, Brassica glycerides, butyrospermum parkii (Shea) butter, benzyl alcohol, *Chondrus crispus* (carrageenan), caprylic/capric triglyceride (and) *Cymbidium grandiflorum* (orchid), *Copernicia cerifera* (Carnauba) wax, coco glucoside, *Cymbopogon flexuosus* leaf oil, cetearyl alcohol (and) cetearyl glucoside, calcium sodium borosilicate, captivates GL or HC, citronellol, cetyl lactate, decyl glucoside, dimethicone, diisopropyl adipate, ethyl cellulose, ethyl paraben, erythritol, ethylhexyl salicylate, *Euphorbia*

*cerifera* (Candelilla) wax, ethylhexyl triazone, ethyl hexyl palmitate, fructose, gelatin, glucose, glyceryl acrylate/acrylic acid copolymer, glyceryl stearate citrate (and) polyglyceryl-3 stearate (and) hydrogenated lecithin, glycerin, glyceryl citrate lactate/linoleate/oleate, hydrolyzed cottonseed extract, inositol, *Helianthus annuus* (Sunflower), *Humulus lupulus* (Hops) extract, 1,2-hexanediol, Isoamyl laurate, isodecyl methylparaben, isocetyl stearoyl stearate, jojoba esters, *Jasminum grandiflorum* flower extract, methyl paraben, maleated soybean oil, glyceryl/octyl dodecanol esters, *Marsdenia cundurango* bark extract, methoxy phenyl triazine, magnesium sulfate heptahydrate, neopentanoate, octyldodecyl stearate, potassium sorbate, phenoxyethanol, propylparaben, polycitronellol acetate, polyglyceryl-3 beeswax, polygylceryl-6 polyhydroxy stearate, polyglyceryl-6-polyricinoleate, raspberry ketone, sodium PCA, sodium benzoate, sucrose, *Santalum album* (sandalwood) wood extract, tetrasodium EDTA, tricontanyl PVP, triethoxycaprylyl silane, tocopherol acetate, trehalose, and zinc oxide.

In another non-limiting embodiment, the present disclosure is directed to a process for preparing an aqueous personal care composition, the process comprising: (a) considering powder particles comprising low substituted carboxymethyl cellulose (CMC) alone or in combination with at least one nature derived polymer or fossil derived polymer; (b) dispersing the powder in water under continuous mixing; (c) subjecting the mixed solution to heating for faster processing; and (c) obtaining the homogenous aqueous composition. The homogenous aqueous composition can be an oil-in-water emulsion, a water-in-oil emulsion, a bead suspension, or a powder suspension.

The oil-in-water emulsion is a gel, a body lotion, a soft body cream, a natural glow serum, a natural sea moisturizer, a frozen mask, a lamellar gel of face cream, a clarifying clay mask, a semi-solid cream, a mineral based sunscreen cream, a daily renewal sunscreen cream, a fluid, a facial lotion, a foundation cream, or a mascara formula.

The present sodium salt of carboxymethyl cellulose (herein referred to as cellulose gum) is nature-derived, biodegradable thickener with suspension capabilities that maintains stability of skin and sun care creams, lotions and gels with a desirable skin feel and texture, offering an alternative to carbomer. It has nature-derived content >84%, readily biodegradable, COSMOS-validation, non-GMO, vegan suitable, clean, simple INCI sustainable sourcing: wood-based cellulose from FSC and PEFC-certified suppliers with zero deforestation practices.

The present cellulose gum brings in multiple benefits including: (i) efficient thickening and suspension properties: effective thickening, suspension capabilities, emulsion stabilizer and enables clear formulations; (ii) desirable skin feel and textures: pleasant skin after-feel, improved aesthetics in comparison to most common natural thickeners; (iii) formulation versatility: electrolytes and minerals tolerant, effective across wide pH range (4-8), no neutralization required, cold processible, compatible with other nature-derived polymers. All these characteristic features make the present cellulose gum a preferred choice for the formulators. Excellent results have been observed for leave-on skin care and hair care applications.

Further, certain aspects of the present application are illustrated in detail by way of the following examples. The examples are given herein for illustration of the application and are not intended to be limiting thereof.

EXAMPLES

Example 1: Carboxymethyl Cellulose Sample Grade

TABLE 1

| CMC Sample Grade | | | |
|---|---|---|---|
| CMC Grade | Viscosity @1% in water (D15 speed 5) cps | Molecular Weight (Daltons) | Degree of Substitution |
| Sample Grade | 8080 | 1640000 | 0.5-0.6 |
| Commercial CMC | 2250 | 1060000 | 0.7-0.8 |

Example 2: Aqueous Suspension Composition

| Ingredients | Quantity (wt. %) |
|---|---|
| Phase A | |
| Purified Water | 85.9 |
| Sample Grade (Cellulose Gum) | 1.5 |
| Phase B | |
| Raspberry Ketone | 0.5 |
| 1,2-Hexanediol | 3.0 |
| Phase C | |
| Water, glycerin, sodium PCA, Erythritol, *chondrus crispus* (carrageenan), Xanthan Gum | 3.0 |
| Phase D | |
| *Aloe Barbadensis* leaf juice powder | 0.1 |
| Water | 1.0 |
| Phase E | |
| Captivates GL or HC | 5.0 |
| Total | 100 |

Example 3: Results of Suspension Stability Studies

Figure 2:
FIG. 2 illustrates suspension studies of comparative CMC vs. inventive CMC sample grades.
Figure 2:
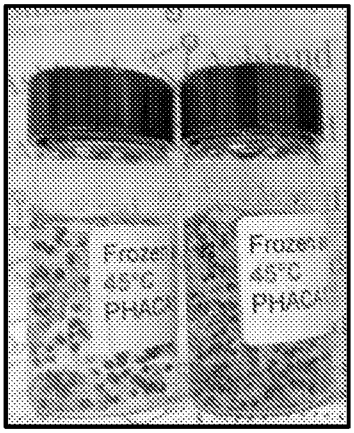
Figure 2:
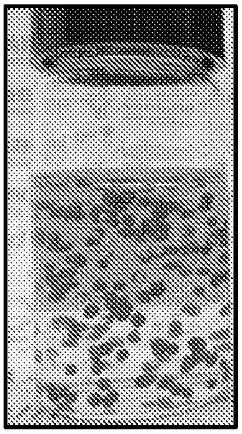
Figure 3:
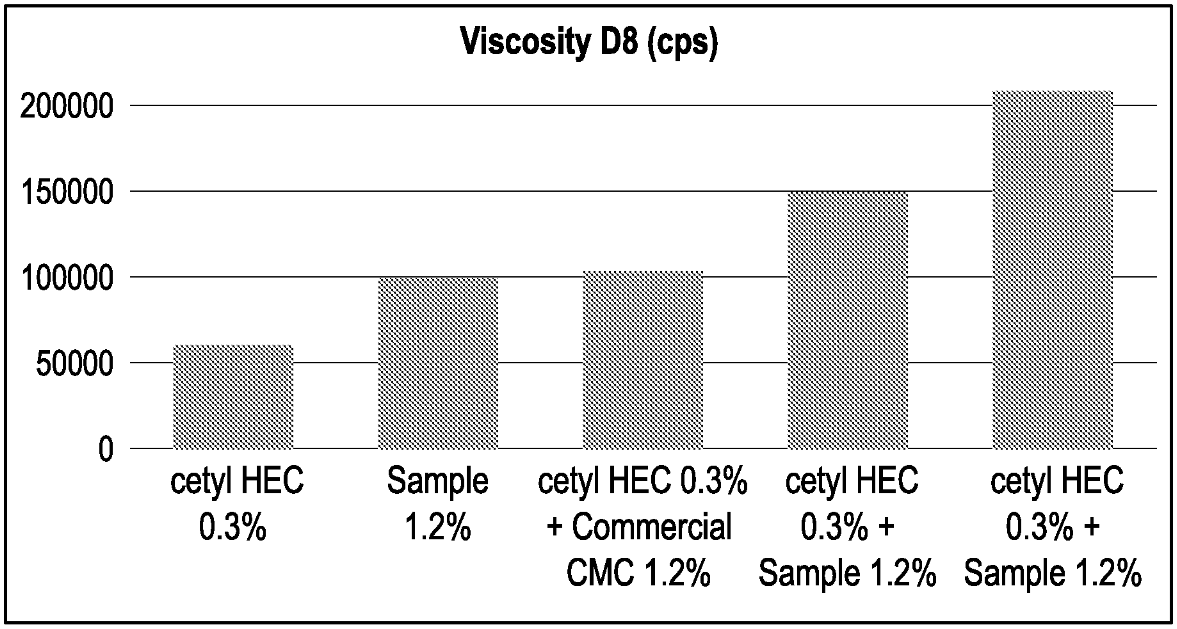
FIG. 3 illustrates viscosity data of comparative CMC vs. inventive CMC—Cetyl HEC combination grades.
Figure 4:
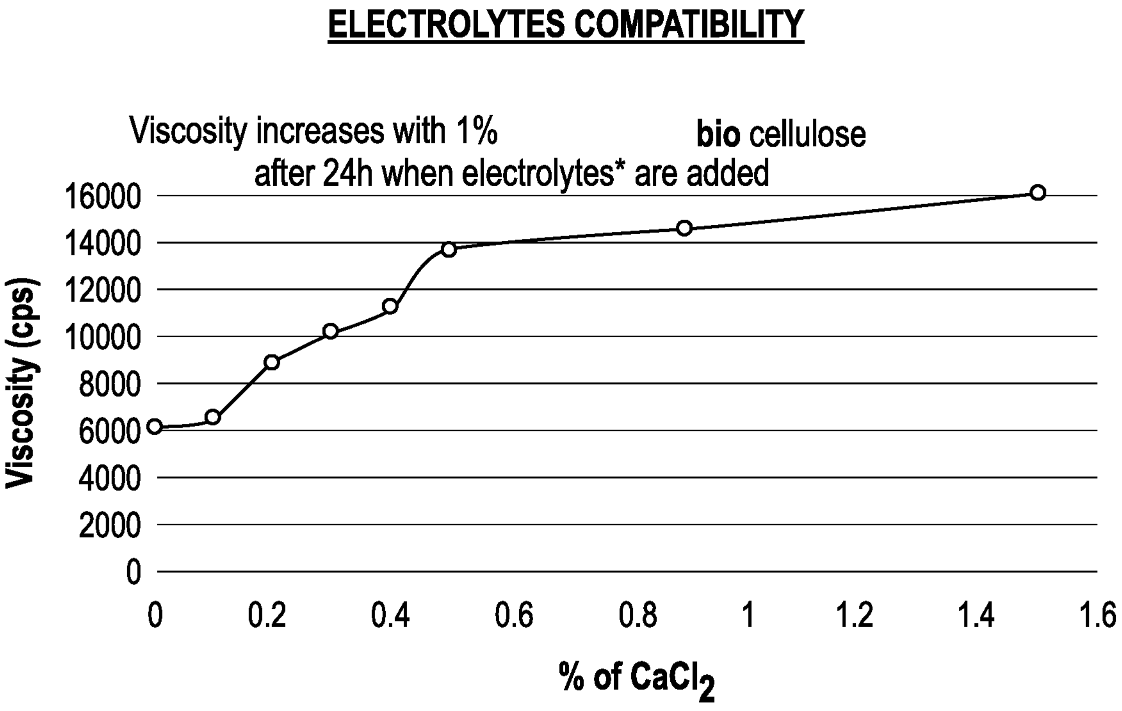
FIG. 4 illustrates compatibility of inventive CMC to electrolytes and minerals.
Figure 4:
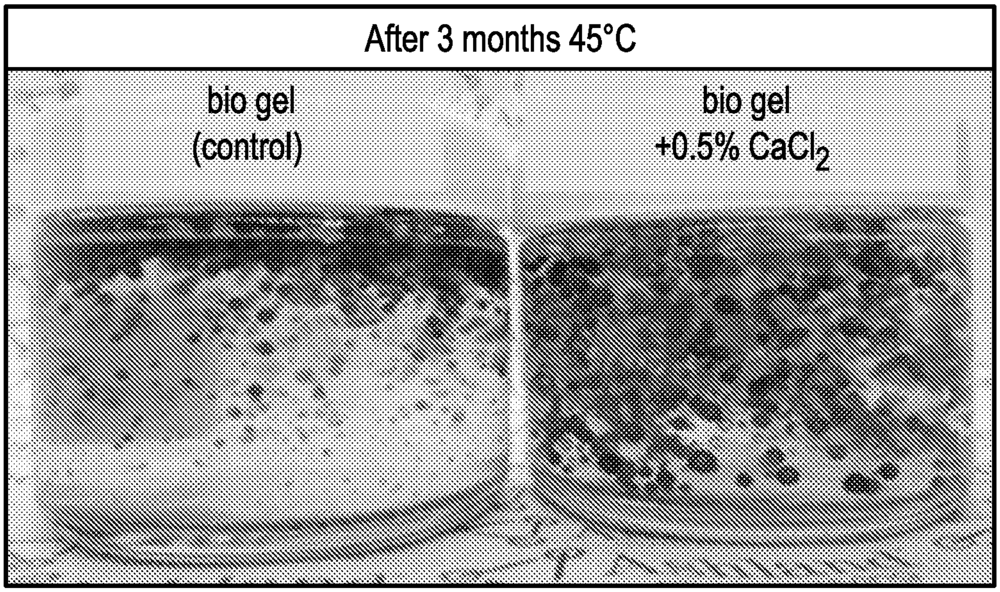

Aqueous suspension described in Example 2 was subjected to suspension studies. The results are shown in FIG. 2. It is observed that 1.5% of commercial CMC, lower amounts of current CMC samples grades (0.5% and 1.0%) either remain at the bottom or on the top of the solution and do not suspend for more than 24 hours at RT. The current sample grades even at higher concentrations (1.5%) remain suspended for three months at 45° C. Concentration of CMC determines the suspension stability.

Example 4: Preparation of Oil-in-Water Emulsion

| Ingredients | Quantity (Wt. %) |
|---|---|
| Phase A | |
| Water/Aqua | Qs. 100 |
| Tetrasodium EDTA | 0.05 |
| Glycerin (and) Glyceryl Acrylate/Acrylic Acid Copolymer (and) Phenoxyethanol | 3.00 |
| Phenoxyethanol (and) Methylparaben (and) Ethyl paraben (and) Propylparaben | 1.00 |
| Phase B | |
| Glyceryl Stearate Citrate (and) Polyglyceryl-3 stearate (and) Hydrogenated lecithin | 2.50 |
| Isodecyl Neopentanoate | 3.00 |
| *Butyrospermum Parkii* (Shea) Butter | 2.00 |
| Isocetyl Stearoyl Stearate | 2.00 |
| Octyldodecyl Stearate | 3.00 |
| Ethylhexyl Palmitate | 4.00 |
| Total | 100.00 |

Example 5: Results of Emulsion Stability Studies

Oil-in-water emulsion prepared using current CMC grades were subjected to stability studies using different emulsifiers and compared against commercial CMC grade. The results are provided below in Table 2.

TABLE 2

Results of oil-in-water emulsion stability

| Emulsifier (2.5%) | Polymer Ingredient | Quantity (%) | Stability |
|---|---|---|---|
| Emulsifier 1 | Cetyl Hydroxyethyl cellulose | 0.3 | passed accelerated stability test |
| | CMC Sample Grade | 1.2 | |
| Emulsifier 1 | CMC Sample Grade | 1.5 | passed accelerated stability test |
| Emulsifier 1 | CMC Sample Grade | 1.5 | passed accelerated stability test |
| Emulsifier 1 | CMC Sample Grade | 1.0 | failed accelerated stability test |
| Emulsifier 1 | CMC Sample Grade | 0.5 | failed accelerated stability test |
| Emulsifier 1 | CMC Sample Grade | 1.5 | failed accelerated stability test |

TABLE 2-continued

Results of oil-in-water emulsion stability

| Emulsifier (2.5%) | Polymer Ingredient | Quantity (%) | Stability |
|---|---|---|---|
| Emulsifier 1 | Commercial CMC | 1.5 | failed accelerated stability test |
| Emulsifier 2 | CMC Sample Grade | 1.5 | passed accelerated stability test |

It was observed that emulsions prepared using sufficient amount of current CMC grades are more stable than those using commercial CMC grade which is broken and therefore less stable.

Example 6: Preparation of Oil-in-Water Emulsion

An oil-in-water emulsion was prepared using carboxymethyl cellulose and ingredients provided below.

| Ingredients | Quantity (Wt. %) |
|---|---|
| Phase A | |
| Water/Aqua | Q.S. to 100 |
| Raspberry Ketone | 0.5 |
| Phenyl propanol (and) *Humulus Lupulus* (Hops) extract | 0.5 |
| Water (and) Glycerin (and) Sodium PCA (and) Erythritol (and) *Chondrus Crispus* (and) Xanthan Gum | 10.0 |
| Phase B | |
| Polymer | 0.3 to 1.50 |
| Phase C | |
| Isodecyl Neopentanoate | 3.00 |
| Cetearyl Alcohol (and) Cetearyl Glucoside | 3.00 |
| *Butyrospermum Parkii* (Shea) Butter | 2.00 |
| Isocetyl Stearoyl Stearate | 2.00 |
| Octyl dodecyl Stearate | 3.00 |
| Ethylhexyl Palmitate | 4.00 |
| Phase D | |
| Allantoin | 0.10 |
| *Aloe Barbadensis* leaf juice powder | 0.10 |
| Total | 100.00 |

Example 7: Results of Emulsion Stability Studies

Oil-in-water emulsions prepared using current CMC grades as in example 6 were subjected to stability studies using various emulsifiers and compared with emulsion prepared using commercial CMC sample. Details are provided below in Table 3.

TABLE 3

Results of oil-in-water emulsion studies

| Emulsifier (2.5 Wt. %) | Polymer Ingredients | Quantity (Wt. %) | Stability |
|---|---|---|---|
| Cetearyl alcohol and Cetearyl Glucoside (non-ionic natural emulsifier) | Cetyl Hydroxyethyl cellulose<br>CMC Sample Grade | 0.3<br>1.2 | passed accelerated stability test |
| Cetearyl alcohol and Cetearyl Glucoside (non-ionic natural emulsifier) | Cetyl Hydroxyethyl cellulose | 0.3 | failed accelerated test |
| Cetearyl alcohol and Cetearyl Glucoside (non-ionic natural emulsifier) | CMC Sample Grade | 1.2 | passed 3 months accelerated stability test |

TABLE 3-continued

| Results of oil-in-water emulsion studies | | | |
|---|---|---|---|
| Emulsifier (2.5 Wt. %) | Polymer Ingredients | Quantity (Wt. %) | Stability |
| Cetearyl alcohol and Cetearyl Glucoside (non-ionic natural emulsifier) | Cetyl Hydroxyethyl cellulose<br>Commercial CMC | 0.3<br>1.2 | failed accelerated stability test |
| Cetearyl alcohol and Cetearyl Glucoside (non-ionic natural emulsifier) | Cetyl Hydroxyethyl cellulose<br>CMC Sample Grade | 0.3<br>1.2 | passed stability test |

Emulsion prepared using emulsifier cetearyl alcohol and cetearyl glucoside based non-ionic natural and inventive CMC samples showed improved emulsion stability.

Example 8; Oil-In-Water Emulsion Gel Cream

An oil-water emulsion gel cream was prepared using fossil derived polymer, low substituted CMC combination and the following ingredients.

| Ingredients | Quantity (Wt. %) |
|---|---|
| Phase A | |
| purified water | Qs. 100 |
| Fossil derived polymer | 0.05 to 0.6 |
| Phase B | |
| inventive polymer | 0 to 1 |
| butylene glycol | 5.0 |
| Phase C | |
| glyceryl citrate lactate/linoleate/oleate | 1.0 |
| isocetyl stearoyl stearate | 3.00 |
| caprylic/capric triglyceride (and) *cymbidium grandiflorum* (orchid) flower extract | 4.00 |
| sodium hydroxide | Qs. (pH 5.2-5.7) |
| benzyl alcohol (and) sodium benzoate (and) potassium sorbate (and) water | 1.0 |
| Total | 100.0 |

Example 9: Water-In-Oil Emulsion

A water-in-oil emulsion gel cream was prepared using the following ingredients.

| Ingredients | Concentrations (wt. %) |
|---|---|
| Phase A | |
| Diisopropyl adipate, ethyl cellulose | 3.0 |
| C13-15 alkane | 10.0 |
| Isoamyl laurate | 16.0 |
| Tricontanyl PVP | 1.0 |
| C12-15 alkyl lactate | 4.0 |

-continued

| Ingredients | Concentrations (wt. %) |
|---|---|
| Phase B | |
| Polygylceryl-6 polyhydroxystearate, Polyglyceryl-6-polyricinoleate, Polyglycerin-6 | 3.0 |
| Phase C | |
| Zinc oxide, triethoxycaprylyl silane | 25.0 |
| Phase D | |
| Water/aqua | 21.5 |
| Butylene glycol | 3.0 |
| Cellulose gum | 0.5 |
| Raspberry ketone | 1.0 |
| Propanediol | 3.0 |
| Magnesium sulfate heptahydrate | 2.0 |
| Water/aqua, glycerin, sodium PCA, erythritol, *chondrus crispus* (carrageenan), xanthan gum | 7.0 |
| Total | 100.0 |

Example 10: Simply Natural Body Lotion

An oil-in-water emulsion of natural body lotion comprising single polymer and low emulsifier was prepared and the ingredients are tabulated below.

| Ingredients | Quantity (Wt. %) |
|---|---|
| Phase A | |
| Water/Aqua | 80.40 |
| Cellulose Gum | 1.30 |
| Phase B | |
| Raspberry Ketone | 0.5 |
| Phase C | |
| Glyceryl Stearate | 0.5 |
| Glyceryl Stearate Citrate (and) Polyglyceryl-3 stearate (and) Hydrogenated lecithin | 1.0 |
| *Butyrospermum Parkii* (Shea) Butter | 2.0 |
| Isocetyl Stearoyl Stearate | 2.0 |
| Octyldodecyl Stearate | 3.0 |
| Ethylhexyl Palmitate | 4.0 |
| Isoamyl Laurate | 3.0 |

-continued

| Ingredients | Quantity (Wt. %) |
|---|---|
| Phase D | |
| Benzyl Alcohol (and) *Cymbopogon Flexuosus* Leaf Oil (and) Tocopherol | 0.8 |
| Phase E | |
| Water/Aqua (and) Glycerin(and) Hydrolyzed Cottonseed extract (and) Trehalose (and) Glucose (and) Fructose (and) Sucrose (and) Inositol | 1.5 |
| Total | 100.00 |

The simple natural body lotion so prepared had a viscosity of 30,000-50,000 cps as measured by Brookfield RVT, Spindle B, 5 RPM, 1 min @ 25° C. and passed the 2-month accelerated lab studies.

Example 11: Soft Body Cream

A soft body cream comprising low amount of combo HMHEC, and high emulsifier was prepared, and the ingredients are tabulated below.

| Ingredients | Quantity (Wt. %) |
|---|---|
| Phase A | |
| Water/Aqua | 79.50 |
| Phase B | |
| Cellulose Gum | 0.4 |
| Cetyl Hydroxyethylcellulose | 0.3 |
| Phase C | |
| Raspberry Ketone | 0.5 |
| Phenyl propanol | 0.8 |
| Phase D | |
| Bis-Stearoxy dimethylsilane (and) Stearyl Alcohol (and) Dimethicone | 2.0 |
| PEG-100 Stearate (and) Glyceryl Stearate | 4.0 |
| *Butyrospermum Parkii* (Shea) Butter | 2.0 |
| Cetyl Lactate | 1.5 |
| Isocetyl Stearoyl Stearate | 2.0 |
| Octyldodecyl Stearate | 3.0 |
| Ethylhexyl Palmitate | 4.0 |
| Total | 100.00 |

The emulsion cream has a viscosity of 110,000-130,000 cps as measured by Brookfield RVT, Spindle C, 5 RPM, 1 min @ 25° C. and passed the 3-month accelerated lab studies.

Example 12: Natural Glow Serum

| Ingredients | Quantity (Wt. %) |
|---|---|
| Phase A | |
| Water/Aqua | 89.40 |
| Cellulose Gum | 1.2 |
| Phase B | |
| Water/Aqua (and) Glycerin (and) Sodium PCA (and) Erythritol (and) *Chondrus Crispus* (Carrageenan) (and) Xanthan Gum | 3.0 |
| Phase C | |
| Calcium Chloride | 0.50 |
| Water/Aqua | 2.00 |
| Phase D | |
| Benzyl Alcohol (and) Sodium Benzoate (and) Potassium Sorbate (and) Water | 1.00 |
| Lactic Acid | 0.40 |
| Phase E | |
| Water (Aqua) (and) *Helianthus Annuus* (Sunflower) Seed Oil (and) Gelatin (and) Acacia Senegal Gum (and) Calcium Sodium Borosilicate (and) Iron Oxides (CI 77491) (and) Tin Dioxide (and) Octyldodecanol (and) *Santalum Album* (Sandalwood) Wood Extract (and) Fragrance (and) Potassium Sorbate (and) Xanthan Gum | 2.50 |
| Total | 100.0 |

Natural glow serum so prepared had a viscosity of 40,000-60,000 cps as measured by Brookfield RVT, Spindle B, 5 RPM, 1 min @ 25° ° C. and passed the 3-month accelerated lab studies.

Example 13: Natural Sea Moisturizer

An oil-in-water natural moisturizer was prepared using the following ingredients.

| Ingredients | Quantity (Wt. %) |
|---|---|
| Phase A | |
| Water/Aqua | 79.062 |
| Phase B | |
| Cellulose Gum | 1.2 |
| Butylene glycol | 5.0 |
| Phase C | |
| Water/Aqua (and) Glycerin (and) Sodium PCA (and) Erythritol (and) *Chondrus Crispus* (Carrageenan) (and) Xanthan Gum | 4.0 |
| Phase D | |
| Caprylic/Capric Triglyceride (and) *Cymbidium Grandiflorum* (Orchid) Flower Extract | 3.00 |
| *Brassica* Glycerides | 2.5 |
| Isocetyl Stearoyl Stearate | 2.0 |
| Glyceryl Citrate/Lactate/Linoleate/Oleate | 1.00 |
| Phase E | |
| Benzyl Alcohol (and) Sodium Benzoate (and) Potassium Sorbate (and) Water/Aqua | 1.00 |
| Lactic Acid | 0.038 |

-continued

| Ingredients | Quantity (Wt. %) |
|---|---|
| Phase F | |
| Water/Aqua (and) Hydrolyzed Collagen | 1.00 |
| fragrance/parfum (and) Benzyl Salicylate (and) Citronellol (and) Hexyl cinnamal (and) Limonene | 0.20 |
| Total | 100.00 |

Natural sea moisturizer so prepared had viscosity of 50,000-70,000 cps measured Brookfield RVT, Spindle B, 5 RPM, 1 min @ 25° C. and further passed the 2 month accelerated lab studies and passed 28 day efficacy challenge test.

Example 14: Frozen Mask

A Frozen Mask of pearls suspension with ethanol compatibility was prepared using the following ingredients.

| Ingredients | Quantity (Wt. %) |
|---|---|
| Phase A | |
| Water/Aqua | 76.23 |
| Cellulose Gum | 1.00 |
| Phase B | |
| Water/Aqua (and) Glycerin (and) Sodium PCA (and) Erythritol (and) *Chondrus Crispus* (Carrageenan) (and) Xanthan Gum | 10.00 |
| Phase C | |
| Raspberry Ketone | 0.50 |
| Menthol | 0.20 |
| Alcohol | 10.00 |
| Phase D | |
| Calcium Aluminium Borosilicate (and) CI 77891 (Titanium Dioxide) (and) Silica (and) Tin Oxide | 0.05 |
| Mica (and) Titanium Dioxide (and) Ferric Ferrocyanide | 0.02 |
| Water/Aqua (and) Propanediol (and) *Jasminum grandiflorum* flower extract | 2.00 |
| Total | 100.00 |

Frozen mask so prepared had viscosity of 20,000-30,000 cps measured Brookfield RVT, Spindle B, 5 RPM, 1 min @ 25° C. and further passed the 1 month accelerated lab studies.

Example 15: Feel the Love Face Cream

An oil-in-water (O/W) lamellar gel system comprising medium amount of HMHEC, and medium emulsifier was prepared using the following ingredients.

| Ingredients | Quantity (Wt. %) |
|---|---|
| Phase A | |
| Water/Aqua | 72.20 |
| Phase B | |
| Cellulose Gum | 0.70 |
| Cetyl Hydroxyethyl cellulose | 0.20 |
| Phase C | |
| Raspberry Ketone | 0.70 |
| Propanediol | 3.00 |
| Phase D | |
| Cetearyl Alcohol (and) Cetearyl Glucoside | 1.00 |
| Arachidy1 Alcohol (and) Behenyl Alcohol (and) Arachidyl Glucoside | 2.00 |
| *Jasminum grandiflorum* flower Cera | 0.10 |
| Glyceryl Dilaurate | 2.00 |
| Isoamyl Laurate | 4.00 |
| Glyceryl Stearate | 2.00 |
| Polycitronellol Acetate | 6.00 |
| Dimethicone | 2.00 |
| Phase E | |
| Allantoin | 0.10 |
| Water/Aqua (and) Propanediol (and) *Jasminum grandiflorum* flower extract | 2.00 |
| Water/Aqua | 2.00 |
| Total | 100.00 |

Feel the Love face cream so prepared had viscosity of 150,000-200,000 cps measured Brookfield RVT, Spindle C, 5 RPM, 1 min @ 25° C. and further passed the 2 month accelerated lab studies.

Example 16: Clarifying Clay Mask

Oil-in-water lamellar gel system with clay compatibility comprising combo HMHEC was prepared using the following ingredients.

| Ingredients | Quantity (Wt. %) |
|---|---|
| Phase A | |
| Water/Aqua | 55.30 |
| Phase B | |
| Cellulose Gum | 0.60 |
| Cetyl Hydroxyethyl cellulose | 0.40 |
| Propanediol | 3.00 |
| Phase C | |
| Glyceryl stearate (and) Cetyl Alcohol (and) stearyl Alcohol (and) behenyl alcohol (and) palmitic acid (and) stearicacid (and) Hydroxyethyl Cetearamidopropyldimonium Chloride | 5.00 |
| Octyldodecyl Stearoyl Stearate | 3.00 |
| Isoamyl Laurate | 5.00 |
| Caprylic/Capric Triglyceride (and) *Cymbidium Grandiflorum* (Orchid) Flower Extract | 3.00 |
| Kaolin (color clay Rosa) | 1.00 |
| Kaolin (color clay Ivory) | 19.00 |

-continued

| Ingredients | Quantity (Wt. %) |
|---|---|
| Phase D | |
| Caprylyl Glycol (and) Glyceryl Caprylate (and) Propanediol | 2.00 |
| Water/Aqua (and) Butylene glycol (and) *Rosa Centifolia* Flower Extract | 1.00 |
| Parfum/Fragrance (and) Citronellol (and) Geraniol (and) Linalool | 0.20 |
| Titanium dioxide (and) Caramine (and) Mica | 0.20 |
| Total | 100.00 |

Clarifying Clay Mask so prepared had viscosity of 220,000-260,000 cps measured Brookfield RVT, Spindle D, 5 RPM, 1 min @ 25° ° C. and further passed the 1 month accelerated lab studies and 28 day challenge efficacy test.

Example 17: Semi-Solid Cream

A semi-solid cream in oil-in-water lamellar gel system using high amount of combo HMHEC and the following ingredients.

| Ingredients | Quantity (Wt. %) |
|---|---|
| Phase A | |
| Water/Aqua | 75.30 |
| Phase B | |
| Cellulose Gum | 1.20 |
| Cetyl Hydroxyethylcellulose | 0.80 |
| Phase C | |
| Glycerin (and) Water/aqua (and) Glyceryl Acrylate/Acrylic Acid Copolymer (and) PVM/MA Copolymer | 3.00 |
| Phenoxyethanol (and) Caprylyl Glycol (and) Sorbic Acid | 1.50 |
| Phase D | |
| Stearic Acid (and) Behenyl Alcohol (and) Glyceryl Stearate (and) Myristyl Alcohol (and) Lauryl Alcohol (and) Cetyl Alcohol (and) Palmitic Acid (and) Lecithin | 4.00 |
| Glyceryl Dilaurate | 3.00 |
| Isoamyl Laurate | 5.00 |
| Octyldodecyl Stearate | 3.00 |
| Behenyl Alcohol | 1.50 |
| Phase E | |
| Fragrance/Parfum (and) Benzyl salicylate (and) Linalool | 0.20 |
| Total | 100.00 |

Semi-solid cream so prepared had viscosity of 200,000-250,000 cps measured Brookfield RVT, Spindle C, 5 RPM, 1 min @ 25° C. and further passed the 1 month accelerated lab studies and 28 day challenge efficacy test.

Example 18: Mineral Based Cream SPF 50

An oil/water lamellar gel system comprising HMHEC, and minerals compatibility was prepared using the following ingredients.

| Ingredients | Quantity (Wt. %) |
|---|---|
| Phase A | |
| Water/Aqua | 50.70 |
| Disodium EDTA | 0.05 |
| Butylene Glycol | 3.00 |
| Cetyl Hydroxyethylcellulose | 0.20 |
| Cellulose Gum | 0.80 |
| Phase B | |
| Raspberry Ketone | 0.50 |
| Propanediol | 0.75 |
| Phenyl propanol | 0.75 |
| Phase C | |
| Isononyl Isononanoate (and) Ethylhexyl Isononanoate | 5.00 |
| Butyl octyl Salicylate | 5.00 |
| Diisopropyl Adipate | 2.00 |
| Glyceryl stearate (and) Cetyl Alcohol (and) stearyl Alcohol (and) behenyl alcohol (and) palmitic acid (and) stearic acid (and) Hydroxyethyl Cetearamidopropyldimonium Chloride | 4.00 |
| Aleated soybean oil glyceryl/octyldodecanol esters | 2.00 |
| C12-15 Alkyl Lactate | 5.00 |
| Octyldodecyl Stearoyl Stearate | 3.00 |
| Titanium Dioxide (and) Alumina (and) Hydrogen Dimethicone | 8.00 |
| Zinc Oxide (and) Triethoxy caprylyl silane | 8.00 |
| *Marsdenia Cundurango* Bark Extract (and) Caprylic/capric Triglycerides | 1.00 |
| Phase D | |
| Fragrance/Parfum | 0.25 |
| Total | 100.00 |

Example 19: Daily Renewal SPF 30 Cream

A sunscreen cream comprising combination of xanthan gum and organic UV filters was prepared using the following ingredients.

| Ingredients | Quantity (Wt. %) |
|---|---|
| Phase A | |
| Water/Aqua | 69.10 |
| Xanthan Gum | 0.20 |
| Cellulose Gum | 1.00 |
| Phase B | |
| Water/Aqua (and) Glycerin (and) Sodium PCA (and) Erythritol (and) *Chondrus Crispus* (Carrageenan) (and) Xanthan Gum | 3.00 |
| Phase C | |
| Raspberry Ketone | 0.50 |
| Phase D | |
| Cetearyl Alcohol (and) Glyceryl Stearate (and) Jojoba Esters (and) *Helianthus Annuus* (Sunflower) Seed Wax (and) Sodium Stearoyl Glutamate (and) Water (and) Polyglycerin-3 | 3.00 |

-continued

| Ingredients | Quantity (Wt. %) |
|---|---|
| Butyl Methoxy dibenzoyl methane | 3.00 |
| Bis-Ethyl hexyloxy phenol Methoxy phenyl Triazine | 3.00 |
| Ethylhexyl Salicylate | 5.00 |
| Ethylhexyl triazone | 3.00 |
| Isoamyl Laurate | 4.00 |
| Docosane | 1.50 |
| Octyl dodecanol (and) *Santalum Album* (Sandalwood) Wood Extract | 1.00 |
| Diisopropyl Adipate | 2.00 |
| Phase E | |
| Propanediol (and) Caprylyl Glycol (and) Capryl hydroxamic acid | 1.50 |
| Fragrance/Parfum (and) Limonene (and) Linalool | 0.20 |
| Total | 100.00 |

Example 20: Fluid o/w Emulsion

A fluid o/w emulsion comprising magnesium aluminium silicate was prepared using the following ingredients.

| Ingredients | Quantity (Wt. %) |
|---|---|
| Phase A | |
| Water/Aqua | 78.30 |
| Phase B | |
| magnesium aluminum silicate | 0.20 |
| Cellulose Gum | 0.50 |
| Preservative | 2.00 |
| Phase C | |
| Cetearyl Alcohol | 1.00 |
| *Butyrospermum Parkii* (Shea) Butter | 2.00 |
| Isocetyl Stearoyl Stearate | 2.00 |
| Octyldodecyl Stearate | 3.00 |
| Ethylhexyl Palmitate | 4.00 |
| Isodecyl Neopentanoate | 3.00 |
| Polyglyceryl-6 Distearate (and) Jojoba Esters (and) Polyglyceryl-3 Beeswax (and) Cetyl Alcohol | 4.00 |
| Total | 100.00 |

Example 21: Facial Lotion

An o/w emulsion facial lotion compatible with pigments was prepared using the following ingredients.

| Ingredients | Quantity (Wt. %) |
|---|---|
| Phase A | |
| Water/Aqua | 73.519 |
| Cellulose Gum | 1.00 |
| Xanthan Gum | 0.20 |
| Phase B | |
| Cetearyl Alcohol (and) Glyceryl Stearate (and) Jojoba Esters (and) *Helianthus Annuus* (Sunflower) Seed Wax (and) Sodium Stearoyl | 2.00 |

-continued

| Ingredients | Quantity (Wt. %) |
|---|---|
| Glutamate (and) Water (and) Polyglycerin-3 | |
| Myristyl Myristate (and) Myristyl Laurate | 2.00 |
| Glyceryl Stearate | 0.70 |
| *Butyrospermum Parkii* (Shea) Butter | 2.00 |
| Isocetyl Stearoyl Stearate | 2.00 |
| Octyl dodecyl Stearate | 3.00 |
| Ethylhexyl Palmitate | 4.00 |
| Isoamyl Laurate | 3.00 |
| Phase C | |
| Yellow iron oxide (and) Isopropyl Titanium Triisostearate (and) Bis-PEG-15 Dimethicone/IPDI Copolymer (and) PEG-2 Soyamine | 0.02 |
| Red Iron Oxide (and) Isopropyl Titanium Triisostearate (and) Bis-PEG-15 Dimethicone/IPDI Copolymer (and) PEG-2 Soyamine | 0.01 |
| Iron II & Iron III oxide (and) Isopropyl Titanium Triisostearate (and) Bis-PEG-15 Dimethicone/IPDI Copolymer (and) PEG-2 Soyamine | 0.001 |
| Titanium Oxide (and) Isopropyl Titanium Triisostearate (and) Bis-PEG-15 Dimethicone/IPDI Copolymer (and) PEG-2 Soyamine | 0.35 |
| Phase D | |
| Caprylyl Glycol (and) Glyceryl Caprylate (and) Propanediol | 2.00 |
| Water/Aqua (and) Propanediol (and) *Jasminum grandiflorum* flower extract | 2.00 |
| Fragrance/Parfum | 0.20 |
| Phase E | |
| Titanium dioxide & mica & silica | 2.00 |
| Total | 100.00 |

Example 22: Foundation Cream

An o/w emulsion of foundation cream compatible with pigments was prepared using the following ingredients.

| Ingredients | Quantity (Wt. %) |
|---|---|
| Phase A | |
| Water/Aqua | q.s. |
| Glycerin | 2.0 |
| Disodium EDTA | 0.1 |
| Cellulose Gum | 0.30 |
| Xanthan Gum | 0.20 |
| Phase B | |
| Phenoxyethanol (and) Caprylyl Glycol (and) Sorbic Acid | 1.50 |
| Phase C | |
| Silica | 1.50 |
| Titanium Dioxide and Isopropyl titanium triisostearate | 8.2 |
| Red Iron Oxide and Isopropyl titanium triisostearate | 0.26 |
| Black Iron Oxide and Isopropyl titanium triisostearate | 0.24 |
| Yellow Iron Oxide and Isopropyl titanium triisostearate | 1.14 |

-continued

| Ingredients | Quantity (Wt. %) |
|---|---|
| Phase D | |
| Glyceryl Stearate (and) laureth-23 | 2.00 |
| Ceteareth-20 | 2.00 |
| C-12-15 Alkyl Lactate | 1.50 |
| Isocetyl Stearate | 0.75 |
| Octocrylene | 8.00 |
| Ethylhexyl Salicylate | 5.00 |
| Avobenzone | 3.00 |
| Dimethicone | 4.00 |
| Dimethicone (Eco) | 5.00 |
| Maleated Soybean Oil Glyceryl/Octyl dodecanol Esters | 4.00 |
| Tridecyl Neopentanoate | 3.00 |
| Water/Aqua (and) Butylene Glycol (and) *Theobroma Cacao* (Cocoa) Seed Extract | 0.01 |
| Total | 100.00 |

Example 23: Mascara Formula

An o/w emulsion of mascara compatible with pigments was prepared using the following ingredients.

| Ingredients | Quantity (Wt. %) |
|---|---|
| Phase A | |
| Water/Aqua | 63.70 |
| Disodium EDTA | 0.1 |

-continued

| Ingredients | Quantity (Wt. %) |
|---|---|
| Cellulose Gum | 0.30 |
| Xanthan Gum | 0.20 |
| Phase B | |
| Iron Oxide | 12 |
| Phase C | |
| Glyceryl Stearate (and) Laureth-23 | 3.00 |
| C18-36 Acid Triglyceride | 4.00 |
| Beeswax | 4.00 |
| Stearic Acid | 2.00 |
| *Copernicia Cerifera* (Carnauba) wax | 2.00 |
| *Euphorbia Cerifera* (Candelilla) wax | 2.00 |
| PEG-20 Stearate | 2.00 |
| Maleated Soybean Oil Glyceryl/Octyl dodecanol Esters | 3.00 |
| Phase D | |
| Tocopheryl acetate | 0.20 |
| 1,2 octanediol, 2-phenoxyethanol | 1.50 |
| Total | 100.00 |

Example 24: Cellulose Concentration Studies: APG Rinse-Off System

Various samples of APG Rinse-Off system comprising the following ingredients were prepared

TABLE 4

| Ingredients | 1 | 2 | 3 | 4 | 5 | 6 | 7 |
|---|---|---|---|---|---|---|---|
| Water/Aqua | 70.00 | 69.50 | 69.40 | 69.30 | 69.20 | 69.10 | 69.00 |
| Cellulose Gum | — | 0.50 | 0.60 | 0.70 | 0.80 | 0.90 | 1.00 |
| Glycerin | 3.00 | 3.00 | 3.00 | 3.00 | 3.00 | 3.00 | 3.00 |
| Decyl Glucoside | 16.00 | 16.00 | 16.00 | 16.00 | 16.00 | 16.00 | 16.00 |
| Coco glucoside | 10.00 | 10.00 | 10.00 | 10.00 | 10.00 | 10.00 | 10.00 |
| Preservative | 1.00 | 1.00 | 1.00 | 1.00 | 1.00 | 1.00 | 1.00 |
| Total | 100.0 | 100.0 | 100.00 | 100.00 | 100.00 | 100.00 | 100.00 |

Example 25: APG Salt Concentration Studies in Rinse-Off System

APG Rinse-Off salt was prepared comprising the following ingredients.

| Ingredients 12896-188 | 1 |
|---|---|
| Water/Aqua | 67.70 |
| Cellulose Gum | 0.80 |
| Glycerin | 3.00 |
| Decyl Glucoside | 16.00 |
| Cocoglucoside | 10.00 |
| Preservative | 1.00 |
| Hole for salt | 1.50 |
| Total | 100.00 |

Various formulation samples of APG Rinse-Off salt using the above rinse off salt comprising the following ingredients were prepared.

TABLE 5

| Ingredients 12896-188 | A | B | C | D | E | F | G |
|---|---|---|---|---|---|---|---|
| Formula 12896-188-1 | 98.50 | 98.50 | 98.50 | 98.50 | 98.50 | 98.50 | 98.50 |
| NaCl | — | 0.25 | 0.50 | 0.75 | 1.0 | 1.25 | 1.50 |
| Deionized water | 1.50 | 1.25 | 1.00 | 0.75 | 0.50 | 0.25 | — |
| Total | 100.00 | 100.00 | 100.00 | 100.00 | 100.00 | 100.00 | 100.00 |

Example 26: Rinse Off—CAPB Single Surfactant

Rinse-off in single surfactant cocamidopropyl betaine (CAPB) was prepared comprising the following ingredients.

TABLE 6

| Ingredients 12896-201 | 1 | 2 |
|---|---|---|
| Water/Aqua | 89.33 | 86.00 |
| Cellulose Gum | 1.00 | 1.00 |
| Glycerin | 2.00 | 2.00 |
| cocamidopropyl betaine | 6.67 | 10.00 |
| sodium benzoate and potassium sorbate in benzyl alcohol | 1.00 | 1.00 |

It was observed that Cellulose Gum is compatible and does thicken the CAPB only system. It was further checked for use in combination with APG to see if the same can be combined into a more complex system. Higher level of CAPB did not result in higher viscosity.

Example 27: Rinse Off—APG System—Suspension

A suspension of APG Rinse-Off was prepared using the following composition.

TABLE 7

| Ingredients 12896-204 | 1 | 2 |
|---|---|---|
| Water/Aqua | 69.20 | 69.00 |
| Cellulose Gum | 0.80 | 1.00 |
| Glycerin | 3.00 | 3.00 |
| Decyl Glucoside | 16.00 | 16.00 |
| Cocoglucoside | 10.00 | 10.00 |
| benzoic and sorbic acids in benzyl alcohol | 1.00 | 1.00 |

TABLE 7-continued

| Ingredients 12896-204 | 1 | 2 |
|---|---|---|
| Captivate encapsulates beads (GL7606) | 0.50 | 0.50 |
| Viscosity | 9200 cps | 23000 cps |

GL 7606 beads - 50% body lotion in matrix of alginate and agar

While the compositions and methods of the disclosed and/or claimed inventive concept(s) have been described in terms of important aspects, it will be apparent to those of ordinary skill in the art that variations may be applied to the compositions and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed! and/or claimed inventive concept(s).

What is claimed is:

1. An aqueous personal care composition comprising:

(a) 0.1 to 10 wt. % of low-substituted carboxymethyl cellulose (CMC) alone or in combination with 0.01 to 10 wt. % of at least one nature-derived polymer or at least one fossil-derived polymer; and (b) 0.01 to 60 wt. % of at least one personal care additive; and (c) water, wherein the low-substituted carboxymethyl cellulose has;

(i) an average degree of carboxymethyl substitution (DS) per anhydroglucose unit in a range of from about 0.5 to about less than 0.65;

(ii) an average viscosity in a range of from about >3000 to about 20000 cps in 1% aqueous solution; and (iii) a molecular weight in a range of from about 1000000 to about 2000000 Daltons; and wherein the low-substituted carboxymethyl cellulose is readily biodegradable.

2. The aqueous personal care composition according to claim 1, wherein the nature-derived polymer is selected from the group consisting of xanthan gum, guar gum, carob gum, konjac gum, sclerotium gum, acacia gum, cellulose gum, pullulan, microcrystalline cellulose, sodium carboxymethyl starch, hydrophobically modified hydroxyethyl cellulose, hydroxypropyl starch phosphate, *Caesalpinia spinosa* gum, carrageenan, dehydroxanthan gum, potato starch modified, glucomannan, magnesium aluminium silicate, bentonite, corn starch modified, polyester based polymer, and gellan Gum.

3. The aqueous personal care composition according to claim 1, wherein the nature-derived polymer is xanthan gum.

4. The aqueous personal care composition according to claim 1, wherein the fossil-derived polymer is an acrylate-based polymer, methacrylate-based polymer, maleic-anhydride based polymer, polyurethane-based polymer, polyester-based polymer, or a vinyl pyrrolidone-based polymer.

5. The aqueous personal care composition according to claim 1, wherein the low-substituted CMC is in the form of a solid particulate or a powder.

6. The aqueous personal care composition according to claim 1, wherein the composition is an emulsion, a dispersion, a suspension, a lotion, a cream, a foam, a spray, a gel, a soap bar, a stick, a mask, a pad, or a patch.

7. The aqueous personal care composition according to claim 6, wherein the emulsion is an oil-in-water emulsion or a water-in-oil emulsion, and the suspension is a bead suspension or a powder suspension.

8. The aqueous personal care composition according to claim 7, wherein the oil-in-water emulsion is a gel, a body lotion, a soft body cream, a natural glow serum, a natural sea moisturizer, a frozen mask, a lamellar gel of face cream, a clarifying clay mask, a semi-solid cream, a mineral-based sunscreen cream, a daily renewal sunscreen cream, a fluid, a facial lotion, a foundation cream, or a mascara formula.

9. The aqueous personal care composition according to claim 8, wherein the gel is stable, imparts high viscosity, and provides an aesthetic feel to the consumer.

10. The aqueous personal care composition according to claim 1, wherein the personal care composition is formulated into a hair-care product, a shampoo, a hair conditioner, leave in and rinse off conditioner, a styling hair composition, a hair perming product, a hair relaxant, a hair straightener, a hair spray and lacquer, a permanent hair dyeing system, a hair styling mousse, a hair gel, a semi-permanent hair dyeing system, a temporary hair dyeing system, a hair bleaching system, a permanent hair wave system, a hair setting formulation, a liquid soap, a bar soap, a fragrance and/or odoriferous ingredients consisting preparation, a deodorizing and antiperspirant preparation, a body oil, a body lotion, a body gel, a treatment cream, a body cleaning product, a skin protection ointment, a shaving and aftershave preparation, a skin powder, a lipstick, a foundation, a nail varnish, an eye shadow, a mascara, a dry and moist make-up, a rouge, a powder, a depilatory agent, a leave-on skin lotion and cream, a shower gel, a toilet bar, a sunless tanner, a sunscreen lotion, a sunscreen spray, a sunscreen cream, a styling gel, a serum, a mask, a sunscreen lotion, dentifrice, and a tooth paste.

11. The aqueous personal care composition according to claim 1, wherein the low-substituted carboxymethyl cellulose is readily biodegradable with 71% biodegradation after 28 days characterized as per OECD Test Method—301D.

12. A process for preparing an aqueous personal care composition the process comprising:

(a) preparing an admixture consisting of powder particles comprising low-substituted carboxymethyl cellulose (CMC) of alone or in combination with at least one nature-derived polymer or at least one fossil-derived polymer with at least one personal care additive and water;

(b) dispersing the powder particles in the admixture under continuous mixing to obtain a mixed solution;

(c) subjecting the mixed solution to heating for faster processing; and (d) obtaining the aqueous personal care composition.

13. The process according to claim 12, wherein the homogenous aqueous composition is an oil-in-water or a water-in-oil emulsion.

14. An aqueous skin care emulsion composition comprising:

(a) 0.1 to 10 wt. % of low-substituted carboxymethyl cellulose (CMC) alone or in combination with 0.01 to 10 wt. % of at least one nature-derived polymer or at least one fossil-derived polymer;

(b) 0.01 to 60 wt. % of at least one skin care additive; and (c) water;

wherein the low-substituted carboxymethyl cellulose has:

(i) an average degree of carboxymethyl substitution (DS) per anhydroglucose unit in a range of from about 0.5 to about less than 0.65;

(ii) an average viscosity in a range of from about >3000 to about 20000 cps in 1% aqueous solution; and (iii) a molecular weight in a range of from about 1000000 to about 2000000 Daltons; and wherein the low-substituted carboxymethyl cellulose is readily biodegradable.

15. The aqueous skin care composition according to claim 14, wherein the emulsion is an oil-in-water emulsion or a water-in-oil emulsion.

16. The aqueous skin care emulsion according to claim 14, wherein the skin care additive is selected from vitamin B compounds, vitamin E compounds, vitamin C compounds, vitamin D compounds, peptides, sugar amines, protease inhibitors, sunscreens, desquamation agents, chelators, skin lightening compounds, non-vitamin antioxidant radical scavengers, phytosterols, plant hormones, protease inhibitors, tyrosinase inhibitors, anti-inflammatory agents, topical anesthetics, anti-cellulite agents, sunless tanning agents, N-acyl amino acid compounds, preservatives, preservative boosters, glycerin, glycol, their derivatives and mixtures thereof.

* * * * *